US012586668B2

(12) United States Patent
Draghi et al.

(10) Patent No.: US 12,586,668 B2
(45) Date of Patent: *Mar. 24, 2026

(54) SYSTEM AND METHOD FOR PATIENT CARE IMPROVEMENT

(71) Applicant: Sanofi, Paris (FR)

(72) Inventors: Ronald Draghi, Islip, NY (US); Michael Hauser, South Portland, ME (US); Brian Stancampiano, Fairport, NY (US)

(73) Assignee: Sanofi, Paris (FR)

( * ) Notice: Subject to any disclaimer, the term of this patent is extended or adjusted under 35 U.S.C. 154(b) by 143 days.

This patent is subject to a terminal disclaimer.

(21) Appl. No.: 18/540,572

(22) Filed: Dec. 14, 2023

(65) Prior Publication Data

US 2024/0120051 A1 Apr. 11, 2024

Related U.S. Application Data

(63) Continuation of application No. 17/738,878, filed on May 6, 2022, now Pat. No. 11,887,711, which is a
(Continued)

(51) Int. Cl.
*G16H 20/10* (2018.01)
*G16H 10/60* (2018.01)
(Continued)

(52) U.S. Cl.
CPC ............. *G16H 15/00* (2018.01); *G16H 10/60* (2018.01); *G16H 40/20* (2018.01); *G16H 40/60* (2018.01); *G16H 40/63* (2018.01)

(58) Field of Classification Search
None
See application file for complete search history.

(56) References Cited

U.S. PATENT DOCUMENTS

2002/0032583 A1 3/2002 Joao
2002/0045808 A1 4/2002 Ford et al.
(Continued)

FOREIGN PATENT DOCUMENTS

EP 1281351 2/2003

OTHER PUBLICATIONS

Cook et al., "Assessing Inpatient Glycemic Control: What are the Next Steps?," Journal of Diabetes Science and Technology, 2012, 6(2): 421-427.
(Continued)

*Primary Examiner* — John A Pauls
(74) *Attorney, Agent, or Firm* — Fish & Richardson P.C.

(57) ABSTRACT

Described is a system comprising an input module receiving a first data set indicative of at least one patient condition for each of a plurality of patients obtained during a predetermined time period, a comparison module comparing each of the at least one patient condition to at least one filter criteria, a filter module selecting a patient to include in a second data set if the at least one patient condition of the patient satisfies the at least one filter criteria, a report module generating a report based on the second data set, wherein the report includes at least one patient identifier for each patient in the second data set and at least one descriptor of the at least one patient condition for each patient in the second data set, and a classification module storing at least one classification value for the at least one patient condition.

20 Claims, 5 Drawing Sheets

Related U.S. Application Data continuation of application No. 16/415,961, filed on May 17, 2019, now Pat. No. 11,328,800, which is a continuation of application No. 13/927,910, filed on Jun. 26, 2013, now Pat. No. 10,339,272.

(51) Int. Cl.

| | |
|---|---|
| *G16H 15/00* | (2018.01) |
| *G16H 40/20* | (2018.01) |
| *G16H 40/60* | (2018.01) |
| *G16H 40/63* | (2018.01) |

(56) References Cited

U.S. PATENT DOCUMENTS

| | | | |
|---|---|---|---|
| 2003/0036683 | A1 | 2/2003 | Kehr et al. |
| 2003/0050794 | A1 | 3/2003 | Keck |
| 2003/0187691 | A1 | 10/2003 | Dutt et al. |
| 2005/0209886 | A1 | 9/2005 | Corkern |
| 2005/0283466 | A1 | 12/2005 | Dettinger et al. |
| 2007/0112261 | A1 | 5/2007 | Enegren et al. |
| 2007/0260491 | A1 | 11/2007 | Palmer et al. |
| 2009/0216555 | A1 | 8/2009 | Mitchell et al. |
| 2010/0088118 | A1 | 4/2010 | Jang et al. |
| 2012/0053436 | A1 | 3/2012 | Sauers et al. |
| 2012/0109687 | A1 | 5/2012 | Tubb |
| 2014/0108033 | A1 | 4/2014 | Akbay et al. |
| 2014/0324445 | A1 | 10/2014 | Carlsgaard et al. |
| 2018/0113994 | A1* | 4/2018 | Sexton ................... G16H 10/60 |

OTHER PUBLICATIONS ncbi.nlm.nih.gov [online], "Adverse Drug Reaction Probability Scale (Naranjo) in Drug Induced Liver Injury"; National Center for Biotechnology Information, May 4, 2019, retrieved on Dec. 18, 2020, retrieved from URL<www.ncbi.nlm.nih.gov/books/NBK548069/>, 7 pages.

* cited by examiner

System 10

Central Computer 100

Remote Computer 200

Remote Computer 200

Remote Computer 200

Central Computer 100

Input Module 105

Comparison Module 110

Filter Module 115

Report Module 120

Storage Module 125

Access Module 130

Alert Module 135

Recommendation Module 140

Progress Module 145

Classification Module 150

Figure 3:
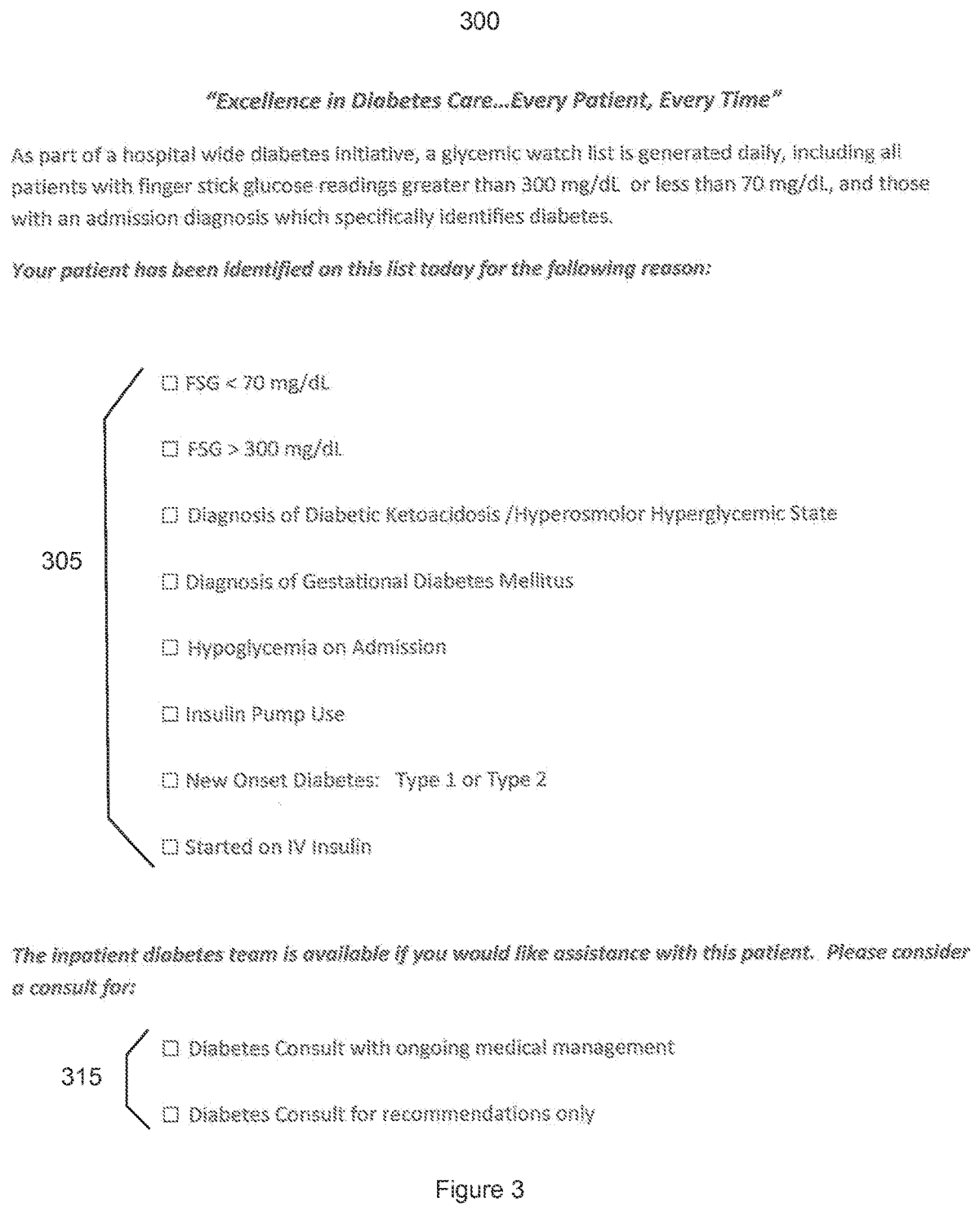

300

*"Excellence in Diabetes Care...Every Patient, Every Time"*

As part of a hospital wide diabetes initiative, a glycemic watch list is generated daily, including all patients with finger stick glucose readings greater than 300 mg/dL or less than 70 mg/dL, and those with an admission diagnosis which specifically identifies diabetes.

*Your patient has been identified on this list today for the following reason:*

305

☐ FSG < 70 mg/dL

☐ FSG > 300 mg/dL

☐ Diagnosis of Diabetic Ketoacidosis /Hyperosmolor Hyperglycemic State

☐ Diagnosis of Gestational Diabetes Mellitus

☐ Hypoglycemia on Admission

☐ Insulin Pump Use

☐ New Onset Diabetes:   Type 1 or Type 2

☐ Started on IV Insulin

*The inpatient diabetes team is available if you would like assistance with this patient. Please consider a consult for:*

315

☐ Diabetes Consult with ongoing medical management

☐ Diabetes Consult for recommendations only

Figure 4:
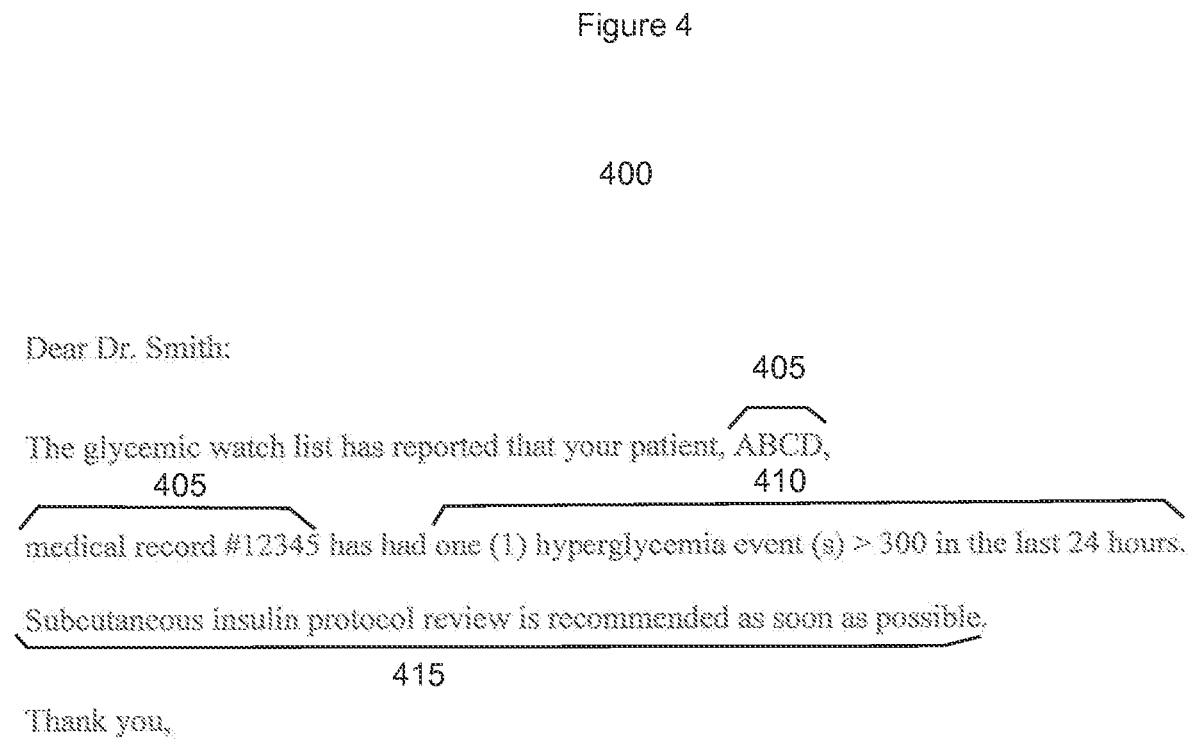

Dear Dr. Smith:

405

The glycemic watch list has reported that your patient, ABCD, 405                                                                    410 medical record #12345 has had one (1) hyperglycemia event (s) > 300 in the last 24 hours.

Subcutaneous insulin protocol review is recommended as soon as possible.

415

Thank you,

Figure 5

500    Glycemic Control Performance Improvement Work Sheet

Patient Sticker

MD: _____    Unit: _____    Date: _____

Below are some of the most common factors contributing to alterations in glycemic control while a patient is in the hospital. Please review your patient's situation and identify possible contributing factors. You may need to collaborate with the physician or MLP or the RN caring for the patient the previous day to accurately identify these factors. Check (√) all that may apply.

| # | Clinical situations which can increase the risk for hypoglycemia and hyperglycemia | Time FSG □ <70 □ >300 | Time FSG □ <70 □ >300 | Time FSG □ <70 □ >300 | Time FSG □ <70 □ >300 | Time FSG □ <70 □ >300 | Time FSG □ <70 □ >300 |
|---|---|---|---|---|---|---|---|
| 1 | Changes in caloric or carbohydrate intake | | | | | | |
| 2 | Change in clinical status or medications , ie steroids | | | | | | |
| 3 | Failure to make adjustments to glycemic therapy when daily glucose patterns fall outside goal range | | | | | | |
| 4 | Use of sliding scale insulin (SSI) as monotherapy for > 48 hours | | | | | | |
| 5 | Time between FSG testing, insulin administration and delivery of meals | | | | | | |
| 6 | Lack of communication during times of transfer to different care teams | | | | | | |
| 7 | Use of long acting sulfonylureas in elderly patients and those with kidney or liver insufficiency | | | | | | |
| 8 | Errors in order writing and transcription | | | | | | |
| 9 | Other: | | | | | | |

510

505

SYSTEM AND METHOD FOR PATIENT CARE IMPROVEMENT

CROSS-REFERENCE TO RELATED APPLICATIONS

This application is a continuation of U.S. patent application Ser. No. 17/738,878, filed May 6, 2022, which is a continuation of U.S. patent application Ser. No. 16/415,961, filed May 17, 2019, now U.S. Pat. No. 11,328,800, which is a continuation of U.S. patent application Ser. No. 13/927, 910, filed Jun. 26, 2013, now U.S. Pat. No. 10,339,272. The entire contents of aforementioned applications are incorporated herein by reference.

TECHNICAL FIELD

The invention relates to systems and methods for patient care improvement.

BACKGROUND OF THE INVENTION

Uncontrolled blood sugar continues to impact organizations (e.g., hospitals) both clinically and financially. The organizations have various ways of measuring and analyzing glycemic management performance (sometimes referred to as "glucometrics"). There are four major problems associated with conventional analysis of glycemic management performance. First, glucose measurements taken when a patient is admitted are typically discarded, because the organization may feel that it was not responsible for the patient pre-admittance. Thus, the organization may feel initial glucose measurement may unfairly bias the analysis of its ability to control its patients' blood sugars. Second, the organization may not be using insulin properly to control the patient's blood sugar. For example, incorrect doses or insulin types may be administered, insulin may be administered at incorrect times or not at all, and/or future doses may not be modified in view of intervening blood glucose results. Third, the organization typically utilizes a retrospective analysis after collecting at least one month of glucose measurement and glycemic management performance data. Fourth, the organization, after performing its retrospective analysis, may take at least one month to implement a change to its glycemic management protocols. By waiting at least one month to collect data and at least one further month to implement a change to the glycemic management protocols, the organization is responding to uncontrolled blood sugar issues with at least a two month delay.

There remains a need for an improved system and method for patient care improvement.

SUMMARY OF THE INVENTION

In an exemplary embodiment, a system for patient care improvement comprises an input module receiving a first data set indicative of at least one patient condition for each of a plurality of patients obtained during a predetermined time period, a comparison module comparing each of the at least one patient condition to at least one filter criteria, a filter module selecting a patient to include in a second data set if the at least one patient condition of the patient satisfies the at least one filter criteria, a report module generating a report based on the second data set, wherein the report includes at least one patient identifier for each patient in the second data set and at least one descriptor of the at least one patient condition for each patient in the second data set, and a classification module storing at least one classification value for the at least one patient condition.

In an exemplary embodiment, the comparison module compares each of the plurality of patients to a predetermined patient type. The filter module may not include a patient to include in the second data set if the patient satisfies the predetermined patient type. The predetermined patient type may be based on patient age and time elapsed since the patient was admitted.

In an exemplary embodiment, the input module includes at least one of a graphical user interface and a database. The graphical user interface includes a website and/or a software program.

In an exemplary embodiment, the at least one patient condition includes at least one of a glucose measurement, an admission diagnosis, and an existence of an insulin pump.

In an exemplary embodiment, the predetermined time period is twenty-four hours. In another exemplary embodiment, the predetermined time period begins at least twenty-four hours after the patient is admitted.

In an exemplary embodiment, the at least one filter criteria includes at least one of a glucose measurement below approximately 70 mg/dL, a glucose measurement above approximately 300 mg/dL, a diagnosis of diabetic ketoacidosis, a diagnosis of a hypersomolor hyperglycaemic state, a diagnosis of gestational diabetes mellitus, a hypoglycaemic state, an existence of an insulin pump, a diagnosis of Type 1 diabetes, a diagnosis of Type 2 diabetes, an existence of intravenously-administered insulin.

In an exemplary embodiment, the at least one patient identifier is not a Health Insurance Portability and Accountability Act (HIPAA) Protected Health Information.

In an exemplary embodiment, the at least one descriptor corresponds to the at least one filter criteria.

In an exemplary embodiment, the system further comprises a storage module storing the report in a database. In an exemplary embodiment, the system further comprises an access module limiting access to the report based on predetermined authorization criteria. In an exemplary embodiment, the predetermined authorization criteria include at least one of a username, a password, a pin number, and a biometric.

In an exemplary embodiment, a healthcare provider identifier is associated with each of the at least one patient identifier in the report. In an exemplary embodiment, the system further comprises an alert module transmitting an alert message to an address associated with the healthcare provider identifier. The alert message may include at least one of the at least one patient identifier and the at least one descriptor.

In an exemplary embodiment, the system further comprises a recommendation module generating a treatment recommendation based on the at least one descriptor for each patient in the second data set. In an exemplary embodiment, the system further comprises a progress module storing the treatment recommendation and a progress value indicative of performance of the treatment recommendation.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 3 shows an exemplary embodiment of an alert message according to the present invention;

FIG. 4 shows another exemplary embodiment of an alert message according to the present invention;

FIG. 5 shows an exemplary embodiment of a patient condition classification form according to the present invention.

Corresponding parts are marked with the same reference symbols in all figures.

DETAILED DESCRIPTION

In an exemplary embodiment, the present invention relates to systems and methods for patient care improvement. Although the exemplary embodiment is described with reference to systems and methods for improving glycemic management in a hospital, those of skill in the art will understand that the systems and methods may be utilized for management of other patient parameters such as, for example, pain management, cardio-vascular, etc., and that the systems and methods of the present invention may be utilized in other clinical (e.g., out-patient clinics, elder care facilities, veterinarians, etc.) and non-clinical settings (e.g., homes, schools). Further, the systems and methods of the present invention may be utilized in human care, as well as animal care.

Figures 1, 2:
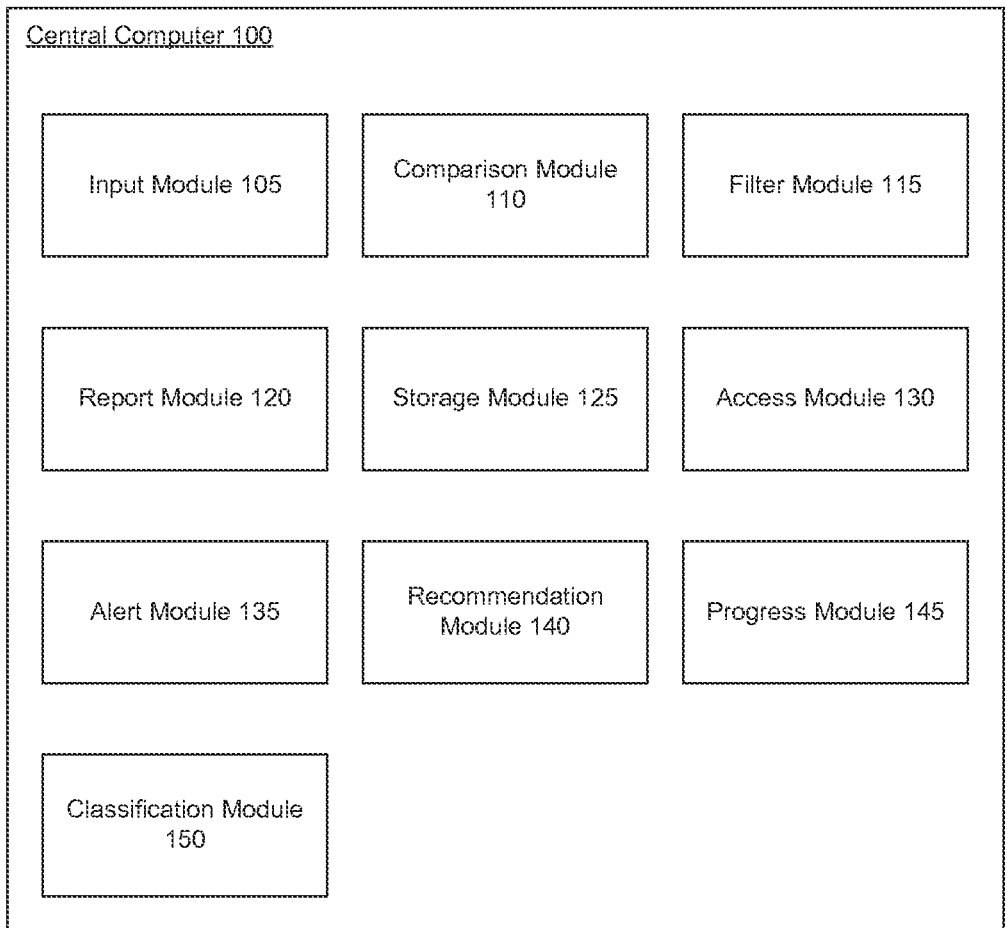
FIG. 1 shows an exemplary embodiment of a system for patient care improvement according to the present invention.
FIG. 2 shows an exemplary embodiment of a central computer according to the present invention.

FIG. 1 shows an exemplary embodiment of a system 10 for patient care improvement according to the present invention. The system 10 may include a central computer 100 which is adapted to communicate with one or more remote computers 200. The central computer 100 may include hardware (e.g., one or more servers, databases, storage media, network communication device, etc.) or software (e.g., one or more software programs), or any combination thereof. The central computer 100 may communicate with the remote computers 200 via wired or wireless communications systems. The remote computers 200 may include PCs, laptops, PDAs, tablets, cellphones, scanners, copiers, printers, kiosks, etc. In an exemplary embodiment, data may be communicated bidirectionally between the central computer 100 and the remote computers 200. In another exemplary embodiment, the remote computers 200 may be used to gather data for transmission to the central computer 100.

In an exemplary embodiment, the system 10 may be implemented in a hospital. For example, the central computer 100 may be a server operated by the hospital, and the remote computers 200 may be associated with individuals (e.g., PDAs of hospital personnel), hospital rooms, hospital areas (e.g., ER, ICU), etc. In an exemplary embodiment, a user of a remote computer 200 may be required to provide authorization information (e.g., username, password, PIN, biometric) to use the remote computer 200 and/or have access to information stored on the central computer 100. In another exemplary embodiment, the hospital personnel may utilize the remote computers 200 to interface with the central computer 100 which may be located outside of the hospital.

FIG. 2 shows an exemplary embodiment of the central computer 100 according to the present invention. The central computer 100 includes an input module 105 adapted to receive a first data set indicative of at least one patient condition for each of a plurality of patients. The at least one patient condition includes at least one of a glucose measurement, an admission diagnosis and an existence of an insulin pump. In an exemplary embodiment, a glucose measurement may be taken by a finger-stick. The admission diagnosis may be determined when a patient is admitted to the hospital. The existence of an insulin pump used by the patient may be determined at a time of admission of the patient or during a time in which the patient is admitted to the hospital.

In an exemplary embodiment, the input module 105 may provide a user interface, e.g., a website or a software program, which is accessible by the remote computers 200. When the patient condition is identified, data identifying the patient condition may be entered into the user interface and uploaded to the central computer 100. For example, a glucose measurement, an admission diagnosis, and/or the existence of an insulin pump for a patient may be entered into an electronic form field and then uploaded to the central computer 100. In another exemplary embodiment, the data identifying the patient condition may be stored in a storage device on the remote computer 200 and uploaded to the central computer 100 at a predetermined time. For example, the remote computers 200 in the hospital may be programmed to upload all of the data collected regarding the patient conditions to the central computer after normal business hours.

In an exemplary embodiment, the data identifying the patient condition(s) for a plurality of patients in the hospital is aggregated by the input module 105 by predetermined time period. For example, the input module 105 may create the first data set by including all data related to patient conditions collected over a 24-hour period. Thus, in this exemplary embodiment, the first data set represents a one-day snapshot of all patient conditions for the patients (or subset thereof) in the hospital.

In an exemplary embodiment, the central computer 100 includes a comparison module 110 that compares the patient condition of each patient in the first data set to at least one filter criteria. For example, the patient condition associated with the first patient entry in the first data set may be compared sequentially or in parallel to one or more of the filter criteria. In an exemplary embodiment, the filter criteria is selected based on the intended patient care improvement. For example, in glycemic control embodiment, the filter criteria may include, but is not limited to, a glucose measurement below approximately 70 mg/dL, a glucose measurement above approximately 300 mg/dL, a diagnosis of diabetic ketoacidosis, a diagnosis of a hypersomolor hyperglycaemic state, a diagnosis of gestational diabetes mellitus, a hypoglycaemic state, an existence of an insulin pump, a diagnosis of Type 1 diabetes, a diagnosis of Type 2 diabetes, an existence of intravenously-administered insulin. Those of skill in the art will understand that the filter criteria may be customized for any metric which is useful for patient care improvement. For example, in a pain management embodiment, the filter criteria may include, but is not limited to, an amount of pain medication taken, a type of pain medication taken, whether the pain medicament was generic, a pain rating by the patient before and/or after taking the pain medication, etc.

In another exemplary embodiment, the comparison module 110 may also compare each patient identified in the first data set to a predetermined patient type. For example, it may be desirable to exclude patient condition data obtained from patients who do not conform to the patient population being analyzed. In one exemplary embodiment, the patient type may be an age threshold (e.g., to exclude children or adults). In another exemplary embodiment, the patient type may be indicative of a duration for which the patient has been admitted (e.g., to exclude patients that have been admitted for less than 24 hours).

In an exemplary embodiment, the central computer 100 includes a filter module 115 which selected a patient identified in the first data set to include in a second data set, which is a subset of the first data set, if the patient condition(s) associated with the patient satisfies at least one of the filter criteria. In the exemplary embodiment, the filter module 115 uses a positive-match inclusion process; however, those of skill in the art will understand that a positive-match exclusion process, a negative-match inclusion process or a negative-match exclusion process may be utilized. For example, if the patient condition is a glucose measurement which is under 70 mg/dL and the filter criteria includes a glucose measurement below approximately 70 mg/dL, the patient may be selected by the filter module 115 for inclusion in the second data set.

Those of skill in the art will understand that the comparison module 110 and the filter module 115 may operate continuously over the predetermined time period to generate the second data set, or may operate once after all of the patient condition data has been collected over the predetermined time period.

In an exemplary embodiment, the central computer 100 includes a report module 120 that generates a report based on the second data set. In an exemplary embodiment, the report may include at least one patient identifier for each patient in the second data set and at least one descriptor of the at least one patient condition for each patient in the second data set. The patient identifier is at least one value that is not a Health Insurance Portability and Accountability (HIPAA) Protected Health Information (PHI). The descriptor may be a text description of the filter criteria, and the descriptor selected for a given patient may correspond to the filter criteria that was satisfied by the patient condition(s) of the given patient. For example, the descriptor may be "FSG<70 mg/dL" to indicate that the patient condition was a glucose measurement that was less than 70 mg/dL, which satisfied the glucose measurement less than 70 mg/dL filter criteria.

The report may be stored by a storage module 125 that saves the report on a storage device within the central computer 100 or a database in communication with the central computer 100.

In an exemplary embodiment, access to the report may be limited. For example, an access module 130 on the central computer 100 may require authorization criteria to access (e.g., view, modify, etc.) the report. The authorization criteria may be entered into the central computer 100 via the input module 105.

In an exemplary embodiment, a healthcare provider (e.g., physician, nurse, out-patient caregiver, family member, etc.) may have an identifier which is associated with each entry in the second data set. For example, a physician identifier (e.g., name, ID number, etc.) may be associated with each patient in the second data set that the physician is responsible for. Thus, the report module 120 can filter and/or sort or the report, or generate a sub-report, that identifies all of the patients in the second data set which a given healthcare provider is responsible for.

In an exemplary embodiment, the central computer 100 includes an alert module 135 for transmitting an alert message to the healthcare provider. For example, if a patient the healthcare provider is responsible for is identified in the second data set, the alert module 135 may generate an alert message identifying the patient using the patient identifier and including the descriptor to inform the healthcare provider about why the patient was included in the second data set. The central computer 100 may include an address (e.g., phone number, fax number, mailing address, email address, instant message address, pager number, etc.) which the alert message is sent to. In an exemplary embodiment, the full alert message is sent to the address of the healthcare provider. In another exemplary embodiment, the alert message may include a hyperlink to the full alert message.

FIG. 3 shows an exemplary embodiment of an alert message 300 according to the present invention. The alert message 300 includes a plurality of descriptor fields 305, and the descriptor(s) that correspond to the patient may be marked.

FIG. 4 shows another exemplary embodiment of an alert message 400 according to the present invention. The alert message 400 includes a patient identifier 405 and a descriptor 410.

Those of skill in the art will understand that the alert message 400 may be generated by a template on the central computer 100 which is populated with information from the second data set.

In an exemplary embodiment, the central computer 100 includes a recommendation module 140 that generates a treatment recommendation based on the descriptor(s) for each patient identified in the second data set. The treatment recommendation may be included in the report and/or the alert message. For example, as shown in FIG. 3, a treatment recommendation 315 may be included in the alert message 300. As shown in FIG. 4, a treatment recommendation 415 may be included in the alert message 400.

In an exemplary embodiment, the treatment recommendation can be determined based on available resources. For example, credentials of healthcare providers, staffing time, patient type, lab value, number/history of e.g., glycyemic events, administrative resources, cause/classification of patient event and day of the week may be considered when generating the treatment recommendation. For example, the recommendation module 140 may analyse the descriptor(s) for a given patient and identify (i) one or more healthcare providers who have expertise in addressing similar patients, (ii) the availability of such healthcare providers, and (iii) the medical history (short-term or long-term) of this patient. The results of this analysis may be used to generate the treatment recommendation.

In an exemplary embodiment, the central computer 100 includes a progress module 145 storing the treatment recommendations for each patient identified in the second data set. The progress module 145 may further include a progress value indicative of performance of the treatment recommendation for a given patient. For example, if a healthcare provider performs a service (e.g., insulin regimen review/modification, consult with other healthcare providers, etc.) identified by and/or associated with the treatment recommendation, the healthcare provider may input treatment data into a remote computer 200 for transmission to the central computer 100. The progress module 145 may compare the treatment data to the treatment recommendation and generate a progress value indicating whether the treatment recommendation was followed. In this manner, the healthcare provider (or any other administrative or monitoring entity) may track the accuracy and efficacy of the treatment recommendations. The report module 120 may be configured to generate a report of the treatment recommendations and progress values for a given patient to, for example, track the impact of the treatment recommendations on a positive or negative outcome on the health and care of the given patient.

In an exemplary embodiment, the central computer 100 includes a classification module 150 for storing at least one classification value for the at least one patient condition. In an exemplary embodiment, the classification module 150 may receive input through manually entered data indicative of possible factors which contributed to an onset of the patient condition. For example, FIG. 5 shows an exemplary embodiment of a patient condition classification form 500 having a plurality of fields. In an exemplary embodiment, the form 500 may be provided by an industry or patient-care group. For example, the form 500 could be a Glycemic Control Performance Improvement Work Sheet provided by the American Association of Clinical Endocrinologists. In another exemplary embodiment, the form 500 may be specially generated for the application. The form 500 may be electronic and implemented on a remote computer 200, providing data to the central computer 100 via the input module 105, or the form 500 may be a hardcopy which is scanned and converted into electronic form for into to the input module 105. For each instance in which a patient condition 510 meets one of the filter criteria, a healthcare provider selects one or more possible factors 505 which contributed to an onset of the patient condition 510. The classification module 150 uses the input provided on the patient condition classification form 500 to generate a classification value for the at least one patient condition. In an exemplary embodiment, the recommendation module 145 may utilize the classification value to generate the treatment recommendation. For example, if the classification value corresponds to a change in caloric intake, the recommendation module 145 may generate a treatment recommendation which suggests raising or lowering the caloric intake for the patient.

In another exemplary embodiment, the classification module 150 may generate the classification value automatically by, for example, analyzing data associated with patient activity, patient eating patterns, patient treatment, patient medication, administrative activity, etc., which may be stored on or accessible by the central computer 100. For example, if a patient condition meets one of the filter criteria, the classification module 150 may analyze the patient's caloric intake for a predetermined time period prior to the onset of the patient condition. If the patient's caloric intake had decreased, relative to previous days, in the twenty-four hours prior to the identification of the patient condition, the classification module 150 may generate a classification value for the patient condition which corresponds to a "change in caloric intake" factor 505. The recommendation module 140 may utilize the classification value to generate a treatment recommendation suggesting that the patient increase her caloric intake (and optionally, include a caloric intake from previous time periods in which the patient condition was not identified). The alert message may include the classification value so that the healthcare provider understands the basis for the treatment recommendation.

While the exemplary embodiment of the central computer 100 describes the various modules as being stored on the central computer 100, in other exemplary embodiments one or more of the modules may be distributed across one or more other computers, and the modules may include or utilize one or more microprocessors and/or storage devices.

Figure 6:
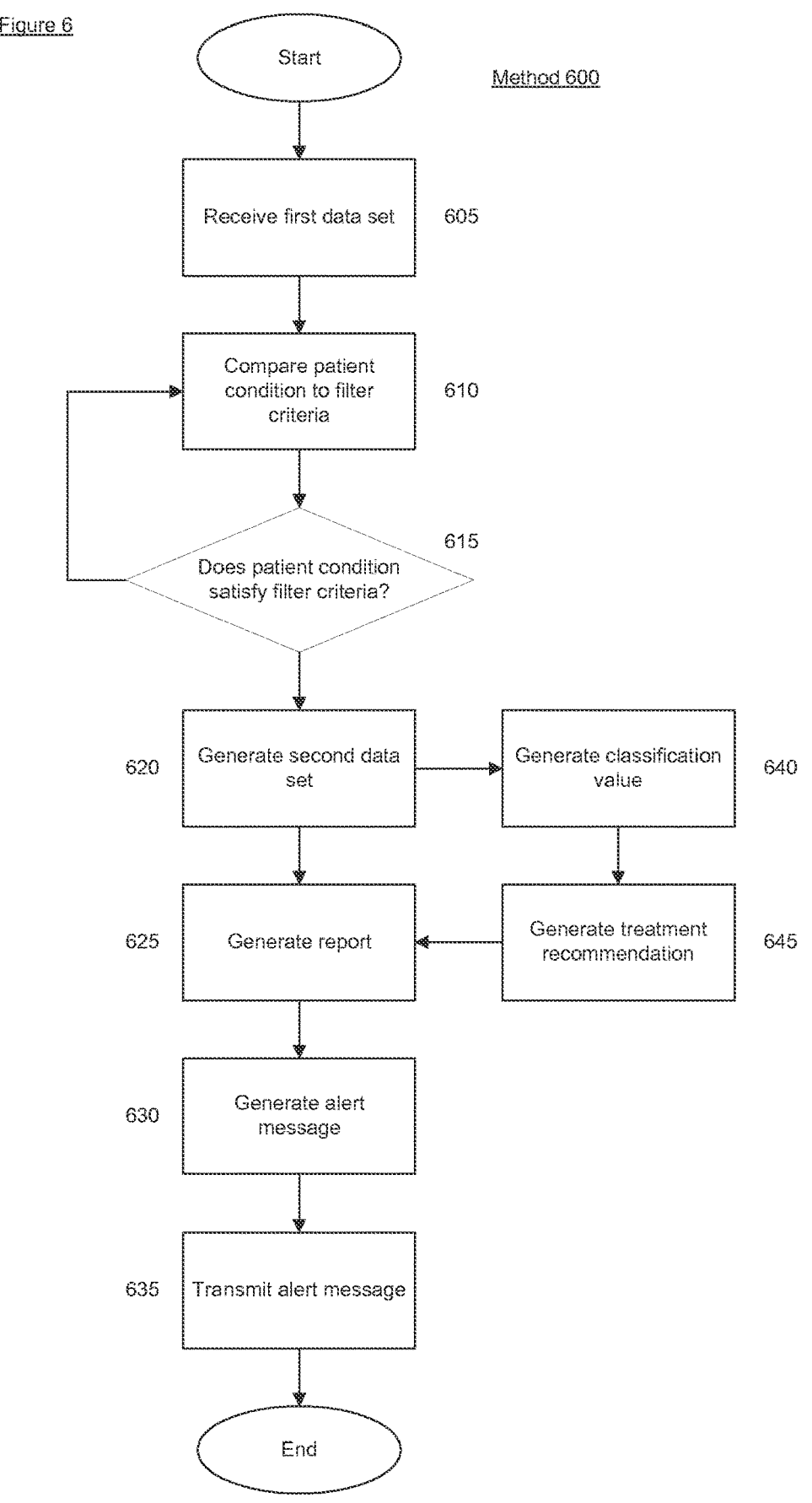
FIG. 6 shows an exemplary embodiment of a method for patient care improvement according to the present invention.

FIG. 6 shows an exemplary embodiment of a method 600 for patient care improvement according to the present invention. The following description of the exemplary method 600 incorporates the description of the structures and algorithms described above.

In step 605, the first data set indicative of at least one patient condition for each of a plurality of patients obtained during a predetermined time period is received. The first data set may be compiled as data regarding patient conditions is received by the central computer 100, or the first data set may be compiled at a predetermined time (e.g., after the predetermined time period has ended).

In step 610, each patient condition in the first data set is compared to at least one filter criteria. Those of skill in the art will understand that such comparison may be string-based comparison using the alphanumeric text of the patient condition and the filter criteria, or the patient condition and the filter criteria may be represented as numbers or short expressions for the comparison.

In steps 615 and 620, the first data set is filtered to generate a second data set by including only patients from the first data set whose patient condition satisfies at least one of the filter criteria. If a given patient condition does not satisfy at least one of the filter criteria, a the patient condition for another patient in the first data set is analyzed until the patient conditions for all of the patients in the first data set have been analyzed. In another exemplary embodiment, the first data set if filtered to generate a second data set by removing patients from the first data set who patient conditions do not satisfy at least one of the filter criteria.

In step 625, a report is generated based on the second data set. In an exemplary embodiment, the report includes at least one patient identifier for each patient in the second data set and at least one descriptor of the at least one patient condition for each patient in the second data set. In step 640, prior to the report being generated, a classification value may be generated and associated with the patient condition for each patient in the second data set. In step 645, prior to the report being generated, a treatment recommendation may be generated and associated with the patient condition for each patient in the second data set. Thus, the report generated in step 625 may include a record for each patient identified in the second data set, and the record may include the patient identifier, the descriptor, the classification value (and/or description) and/or the treatment recommendation.

In steps 630 and 635, an alert message may be generated and transmitted to a healthcare provider associated with a given patient identified in the second data set. The alert message may include any or all of the information in the report.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:
1. A method for glycemic management, the method comprising:
    receiving, by one or more processors, from a plurality of remotely located computers, a first data set that comprises at least one patient condition for each of a plurality of patients, wherein the first data set is obtained during a predetermined time period;

filtering, by the one or more processors, the first data set to create a second data set by comparing a glucose measurement for each patient to at least one filter criterion, wherein the at least one filter criterion comprises the glucose measurement being above a threshold amount relative to a particular age threshold, wherein filtering the first data set to create the second data set comprises, for each of the plurality of patients:
    selecting the patient for inclusion in the second data set only if the glucose measurement for the patient is above the threshold amount relative to the particular age threshold;
generating, by the one or more processors, a treatment recommendation for at least one or more patients of the plurality of patients selected for inclusion in the second data set, wherein the treatment recommendation comprises a recommendation of administering a dose of glucose control medication to the patient based on the at least one filter criterion; and
administering, based at least in part on the treatment recommendation, the dose of glucose control medication to the patient.

2. The method of claim 1, wherein for each of the at least one or more patients of the plurality of patients selected for inclusion in the second data set, generating the treatment recommendation for the patient comprises:
    automatically accessing medical history data for the patient;
    processing the medical history data for the patient, by a classification module, to generate a classification value; and
    determining the treatment recommendation for the patient based on the classification value.

3. The method of claim 1, further comprising, for each of one or more patients selected for inclusion in the second data set:
    generating, based at least in part on the treatment recommendation for the patient and a medical history of the patient, a progress value characterizing efficacy of glycemic management for the patient.

4. The method of claim 1, wherein the treatment recommendation comprises a recommendation of administering a dose of insulin to the patient, wherein the dose of insulin is determined based at least in part on the at least one patient condition that corresponds to at least one classification value.

5. The method of claim 1, further comprising generating a report based on the second data set, wherein the report includes at least one patient identifier for each patient selected for inclusion in the second data set.

6. The method of claim 5, wherein the report further includes a healthcare provider identifier associated with the at least one patient condition.

7. The method of claim 1, wherein for each of the at least one or more patients of the plurality of patients selected for inclusion in the second data set, the alert message includes at least one patient identifier.

8. The method of claim 1, wherein the at least one patient condition includes a glucose measurement.

9. The method of claim 1, wherein the at least one filter criterion includes a glucose measurement threshold.

10. The method of claim 1, further comprising excluding, from the second data set, patients who satisfy a predetermined patient type.

11. The method of claim 1, wherein the at least one patient condition includes at least one of an admission diagnosis or an existence of an insulin pump.

12. The method of claim 1, wherein the predetermined time period begins at least twenty-four hours after the patient is admitted to a medical facility.

13. The method of claim 1, wherein for at least one of the plurality of patients, selecting the patient for inclusion in the second data set comprises determining that a glucose measurement for the patient is above approximately 300 mg/dL.

14. The method of claim 1, wherein the at least one filter criterion includes a diagnosis of diabetic ketoacidosis.

15. The method of claim 1, wherein the at least one filter criterion includes a diagnosis of a hypersomolor hyperglycaemic state.

16. The method of claim 1, wherein the at least one filter criterion includes at least one of: a diagnosis of gestational diabetes mellitus, a hypoglycaemic state, or an existence of an insulin pump.

17. The method of claim 1, wherein the at least one filter criterion includes a diagnosis of Type 1 diabetes.

18. The method of claim 1, wherein the at least one filter criterion includes a diagnosis of Type 2 diabetes.

19. A system comprising:
    one or more computers; and
    one or more storage devices communicatively coupled to the one or more computers, wherein the one or more storage devices store instructions that, when executed by the one or more computers, cause the one or more computers to perform operations for glycemic management, the operations comprising:
    receiving, from a plurality of remotely located computers, a first data set that comprises at least one patient condition for each of a plurality of patients, wherein the first data set is obtained during a predetermined time period;
    filtering the first data set to create a second data set by comparing a glucose measurement for each patient to at least one filter criterion, wherein the at least one filter criterion comprises the glucose measurement being above a threshold amount relative to a particular age threshold, wherein filtering the first data set to create the second data set comprises, for each of the plurality of patients:
        selecting the patient for inclusion in the second data set only if the glucose measurement for the patient is above the threshold amount relative to the particular age threshold;
    generating a treatment recommendation for at least one or more patients of the plurality of patients selected for inclusion in the second data set, wherein the treatment recommendation comprises a recommendation of administering a dose of glucose control medication to the patient based on the at least one filter criterion; and
    generating an output to cause administering, based at least in part on the treatment recommendation, the dose of glucose control medication to the patient.

20. One or more non-transitory computer storage media storing instructions that when executed by one or more computers cause the one or more computers to perform operations for glycemic management, the operations comprising:
    receiving, from a plurality of remotely located computers, a first data set that comprises at least one patient condition for each of a plurality of patients, wherein the first data set is obtained during a predetermined time period;
    filtering the first data set to create a second data set by comparing a glucose measurement for each patient to at least one filter criterion, wherein the at least one filter criterion comprises the glucose measurement being above a threshold amount relative to a particular age threshold, wherein filtering the first data set to create the second data set comprises, for each of the plurality of patients:

selecting the patient for inclusion in the second data set only if the glucose measurement for the patient is above the threshold amount relative to the particular age threshold;

generating a treatment recommendation for at least one or more patients of the plurality of patients selected for inclusion in the second data set, wherein the treatment recommendation comprises a recommendation of administering a dose of glucose control medication to the patient based on the at least one filter criterion; and generating an output to cause administering, based at least in part on the treatment recommendation, the dose of glucose control medication to the patient.

\*　\*　\*　\*　\*